United States Patent
Hayes, Jr. et al.

(10) Patent No.: US 7,189,262 B2
(45) Date of Patent: **\*Mar. 13, 2007**

(54) BIMETAL TIBIAL COMPONENT CONSTRUCT FOR KNEE JOINT PROSTHESIS

(75) Inventors: Daniel E. E. Hayes, Jr., Placerville, CA (US); Alfred S. Depres, III, Shingle Springs, CA (US)

(73) Assignee: Hayes Medical, Inc., Eldorado Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/721,830

(22) Filed: Nov. 25, 2003

(65) Prior Publication Data

US 2004/0267371 A1      Dec. 30, 2004

Related U.S. Application Data

(63) Continuation of application No. 09/910,646, filed on Jul. 19, 2001, now Pat. No. 6,652,588, which is a continuation of application No. 09/901,310, filed on Jul. 9, 2001, which is a continuation of application No. 09/079,502, filed on May 14, 1998, now Pat. No. 6,261,322.

(60) Provisional application No. 60/219,961, filed on Jul. 20, 2000.

(51) Int. Cl.
*A61F 2/38*      (2006.01)
(52) U.S. Cl. .................................. 623/20.32
(58) Field of Classification Search .. 623/20.32–20.36, 623/23.51, 23.53
See application file for complete search history.

(56) References Cited

U.S. PATENT DOCUMENTS

| 3,855,638 | A | 12/1974 | Pilliar |
| 3,953,899 | A | 5/1976 | Charnley |
| 4,166,292 | A | 9/1979 | Bokros |
| 4,216,549 | A | 8/1980 | Hillberry et al. |
| 4,718,905 | A | 1/1988 | Freeman |
| 4,818,559 | A | 4/1989 | Hama et al. |
| 4,978,358 | A | 12/1990 | Bobyn |
| 5,133,771 | A | 7/1992 | Duncan et al. |
| 5,176,712 | A | 1/1993 | Homsy |
| 5,310,408 | A | 5/1994 | Schryver et al. |

(Continued)

FOREIGN PATENT DOCUMENTS

EP      0 925 765 B1    6/1999

(Continued)

*Primary Examiner*—Suzette J-J Gherbi
(74) *Attorney, Agent, or Firm*—Pandiscio & Pandiscio

(57) ABSTRACT

A prosthetic tibial component for a prosthetic total knee joint includes two constructs, one being a metal base that engages a bone and the other being a polyethylene bearing that attaches to the metal base and articulates with a femoral prosthetic component on a opposing side of the joint. The metal base is composed of two metals, one of which engages the bone surface and the other of which engages the polyethylene bearing. Each of the metals is selected for its function. The first metal is selected to provide a superior bone-engaging face, while the second metal is selected to provide a superior polyethylene-engaging face. By combining the different material characteristics of two different metals there is formed a superior bone-engaging face and a superior polyethylene-engaging face.

7 Claims, 3 Drawing Sheets

U.S. PATENT DOCUMENTS

| | | | |
|---|---|---|---|
| 5,323,954 A | 6/1994 | Shetty et al. | |
| 5,372,130 A | 12/1994 | Stern et al. | |
| 5,441,537 A | 8/1995 | Kenna | |
| 5,443,523 A | 8/1995 | Mikhail | |
| 5,545,227 A | 8/1996 | Davidson et al. | |
| 5,549,683 A * | 8/1996 | Bonutti | 623/20.33 |
| 5,569,308 A | 10/1996 | Sottosanti | |
| 5,603,338 A | 2/1997 | Beaty | |
| 5,650,108 A | 7/1997 | Nies et al. | |
| 5,658,338 A | 8/1997 | Tullos et al. | |
| 5,665,118 A | 9/1997 | LaSalle et al. | |
| 5,665,121 A | 9/1997 | Gie et al. | |
| 5,702,448 A | 12/1997 | Buechel et al. | |
| 5,702,461 A | 12/1997 | Pappas et al. | |
| 5,702,466 A | 12/1997 | Pappas et al. | |
| 5,711,763 A | 1/1998 | Nonami et al. | |
| 5,723,011 A | 3/1998 | Devanathan et al. | |
| 5,725,597 A | 3/1998 | Hwang | |
| 5,746,272 A | 5/1998 | Mastrorio et al. | |
| 5,820,707 A * | 10/1998 | Amick et al. | 148/669 |
| 5,824,104 A * | 10/1998 | Tuke | 623/20.32 |
| 5,868,796 A | 2/1999 | Buechel et al. | |
| 5,876,453 A | 3/1999 | Beaty | |
| 5,876,454 A | 3/1999 | Nanci et al. | |
| 5,879,404 A | 3/1999 | Bateman et al. | |
| 5,938,702 A | 8/1999 | Lopez et al. | |
| 5,981,827 A | 11/1999 | Devlin et al. | |
| 5,998,024 A | 12/1999 | Frey et al. | |
| 6,008,432 A | 12/1999 | Taylor | |
| 6,010,533 A | 1/2000 | Pope et al. | |
| 6,045,581 A | 4/2000 | Burkinshaw | |
| 6,083,570 A | 7/2000 | Lemelson et al. | |
| 6,087,553 A | 7/2000 | Cohen et al. | |
| 6,096,175 A | 8/2000 | Roth | |
| 6,120,545 A * | 9/2000 | Hamelijnck et al. | 623/22.15 |
| 6,139,585 A | 10/2000 | Li | |
| 6,165,616 A | 12/2000 | Lemelson et al. | |
| 6,171,343 B1 | 1/2001 | Dearnaley et al. | |
| 6,228,471 B1 | 5/2001 | Neerinck et al. | |
| 6,248,811 B1 | 6/2001 | Ottersbach et al. | |
| 6,261,322 B1 | 7/2001 | Despres, III et al. | |
| 6,291,070 B1 | 9/2001 | Arpac et al. | |
| 6,352,560 B1 * | 3/2002 | Poeschmann et al. | 623/23.4 |
| 6,368,354 B2 | 4/2002 | Burstein et al. | |
| 6,419,707 B1 * | 7/2002 | Leclercq | 623/20.33 |
| 6,447,550 B1 | 9/2002 | Hunter et al. | |
| 6,527,919 B1 | 3/2003 | Roth | |

FOREIGN PATENT DOCUMENTS

| | | |
|---|---|---|
| WO | WO 92/08424 A1 | 5/1992 |
| WO | WO 97/16137 A1 | 5/1997 |
| WO | WO 01/24741 A1 | 4/2001 |

* cited by examiner

BIMETAL TIBIAL COMPONENT CONSTRUCT FOR KNEE JOINT PROSTHESIS

REFERENCE TO PENDING PRIOR APPLICATIONS

This application:

(1) is a continuation of pending prior U.S. patent application Ser. No. 09/910,646, now U.S. Pat. No. 6,652,588, filed Jul. 19, 2001 by Daniel E. E. Hayes, Jr. et al. for BIMETAL TIBIAL COMPONENT CONSTRUCT FOR KNEE JOINT PROSTHESIS; and (2) is a continuation of pending prior U.S. patent application Ser. No. 09/901,310, filed Jul. 09, 2001 by Alfred S. Despres III et al. for IMPLANT WITH COMPOSITE COATING which is in turn a continuation of prior U.S. patent application Ser. No. 09/079,502, now U.S. Pat. No. 6,261,322, filed May 14, 1998 by Alfred S. Despres III et al. for IMPLANT WITH COMPOSITE COATING, and claims the benefit of prior U.S. Provisional Patent Application Ser. No. 60/219,961, filed Jul. 20, 2000 by Daniel E. E. Hayes, Jr. et al. for BIMETAL TIBIAL COMPONENT CONSTRUCT.

The four above-identified patent applications are hereby incorporated herein by reference.

FIELD OF THE INVENTION

This invention relates to surgical apparatus and procedures in general, and more particularly to orthopedic prostheses for restoring the knee joint.

BACKGROUND OF THE INVENTION

Joint replacement surgery seeks to replace portions of a joint with prosthetic components so as to provide long-lasting function and pain-free mobility.

For example, in the case of a prosthetic total hip joint, the head of the femur is replaced with a prosthetic femoral stem component, and the socket of the acetabulum is replaced by a prosthetic acetabular cup component, whereby to provide a prosthetic total hip joint.

In the case of a prosthetic total knee joint, the top of the tibia is replaced by a prosthetic tibial component, and the bottom of the femur is replaced by a prosthetic femoral component, whereby to provide a prosthetic total knee joint.

The present invention is directed to orthopedic prostheses for restoring the knee joint and, in particular, to improved prosthetic tibial components.

There is a long and varied history in the use of different materials for joint replacement prostheses. Some early attempts, such as stainless steel hip prostheses, were found to be reasonably successful and are still in use today. Other attempts, such as acrylic femoral head replacements or Teflon "TMJ" replacements, were found to be unacceptable and have been abandoned.

Currently, combinations of materials are generally used to form joint replacement prostheses.

More particularly, in the case of a prosthetic total hip joint, the prosthetic femoral stem component typically comprises a metal, and the prosthetic acetabular cup component typically comprises a metal seat with a plastic liner.

In the case of a prosthetic total knee joint, the prosthetic tibial component typically comprises a metal base topped with a plastic bearing surface, and the prosthetic femoral component typically comprises a metal.

The present state of the art is currently dominated by the use of three different materials: titanium and its alloys, cobalt-based alloys and polyethylene plastics. The two metallic materials are generally used for structural constructs (e.g., constructs that must carry the loads transmitted through the joint), and polyethylene is generally used as a bearing material in the joints (e.g., to slide or rotate against an opposing metallic component).

Ceramic bearing couples have also been used in the art to some extent, but their use is relatively limited due to price and strength considerations.

The vast majority of structural implant constructs are currently made from either titanium alloys (e.g., Ti6Al4V) or cobalt-based alloys (e.g. CoCr alloys, including CoCrMo alloys). These materials have different advantages and disadvantages.

More particularly, titanium alloys generally exhibit relatively high general fatigue strength, relatively low stiffness compared to alternative materials, and excellent biocompatibility properties. Titanium alloys, however, also tend to suffer from notch sensitivity in fatigue, which significantly reduces the fatigue strength of the construct when the surface is notched, roughened or porous-coated. Titanium alloys are also prone to scratching and make relatively poor sliding couples with polyethylene.

CoCr alloys generally have relatively high fatigue strengths, are relatively notch insensitive, and are relatively tough and resistant to scratching, thus making them excellent candidates for forming sliding couples with polyethylene. However, CoCr alloys are also relatively stiff, which can cause load pattern problems when coupled with flexible human bones, and they are not as biocompatible as many other alloys due to their chrome, and in some cases nickel, content.

In the 1980's, titanium alloys were used in many applications to take advantage of their biocompatibility. However, the applications that included sliding surfaces, such as femoral heads for the hip and knee femoral components, tended to have significant problems with wear debris and scratching, and many exhibited clinical failure.

From this experience, implants were developed that combined the two aforementioned materials (i.e., titanium and CoCr alloys) in advantageous ways.

One early product was a knee femoral component that had a sliding surface of CoCr and a bone ingrowth surface of titanium. This design took advantage of CoCr's excellent wear characteristics in sliding articulations with the tibial component's polyethylene bearing, while still providing excellent bone ingrowth at the bone/prosthesis junction.

The aforementioned two materials (i.e., titanium and CoCr alloys) have also been used on hip femoral stem components. More particularly, hip femoral stem components have been developed which comprise an inner core of CoCr covered with a coating of titanium for bone ingrowth. This layered construction is desirable because stems made entirely of titanium, with titanium ingrowth surfaces, are too weak, while stems that are made entirely of CoCr, with CoCr ingrowth surfaces, do not have adequate biocompatibility. The combination of these two materials in a single construct provides a stem that is strong enough and also has a good bone ingrowth surface.

Another attempt to improve the biocompatibility of the bone ingrowth surface has been to coat the surface with hydroxyapatite (HA). However, HA, while it yields excellent short term results, has problems with long term stability due to its pH sensitivity. More particularly, the pH of the body may fluctuate due to a variety of conditions such as nutrition and disease, and this can undermine the effectiveness of HA bone ingrowth surface.

Another attempt to increase the hardness of the articulating surface has been to coat the articulating surface with a ceramic such as titanium nitride. The main limitation to this approach is that loading and abrading tend to undermine the mechanical integrity of the union between the ceramic coating and the substrate, and this can lead to prosthesis failure.

As wear issues relating to the main articulating surfaces have been addressed and incidences of gross and catastrophic wear eliminated, it has been discovered that the locking interface between the polyethylene bearing construct and the metal base construct can also be a significant source of wear debris. More particularly, it has been discovered that sliding motions in the junction between the polyethylene bearing construct and the metal base construct produce particles of polyethylene that can migrate out of the joint and into the body. Small abrasive particles can also migrate into the interface between the polyethylene bearing construct and the metal base construct and scratch the metal base construct, particularly where the metal base construct is formed out of titanium. This issue of "backside wear" has been a significant issue for research and debate over the last five years or so.

Attempts to address this issue have, to date, been limited to polishing the titanium mating surface of the metal base construct, as disclosed in U.S. Pat. No. 5,310,408 and as practiced in the "Reflection Cup" product marketed by Smith + Nephew of Memphis, Tenn. However, polishing a titanium surface has not worked well in previous attempts in sliding couples (i.e., in the femoral head component of a prosthetic total hip and in the prosthetic femoral component of a prosthetic total knee), and it has had only limited success in reducing wear debris at the locking interface between the polyethylene bearing construct and the metal base construct. This is primarily due to the inherent material limitations of the titanium metal base construct in the polished locking mechanism configuration.

No existing metallic construct that assembles with a polyethylene bearing is made of two metals (i.e., is bimetallic).

No existing bimetallic constructs lock with polyethylene.

SUMMARY OF THE INVENTION

This invention provides for a novel orthopedic prosthesis, specifically a prosthetic tibial component for a prosthetic total knee joint, that comprises two constructs, one being a metal base construct that engages the bone and the other being a polyethylene bearing construct that attaches to the metal base construct and articulates with a prosthetic femoral component on the opposing side of the joint. The metal base construct is composed of two different metals, one of which engages the bone surface and the other of which engages the polyethylene bearing construct. Each of these metals is selected so that its characteristics are well suited to its particular function. More particularly, the first metal (i.e., the one that engages the bone surface) is selected so as to provide a superior bone-engaging face, while the second metal (i.e., the one that engages the polyethylene bearing construct) is selected so as to provide a superior polyethylene-engaging face. By combining the different material characteristics of two different metals in the metal base construct, it is possible to simultaneously form a superior bone-engaging face and a superior polyethylene-engaging face. Among other things, by selecting two appropriate metals for the metal base construct, superior bone ingrowth can be achieved while still avoiding the aforementioned problems with "backside wear".

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
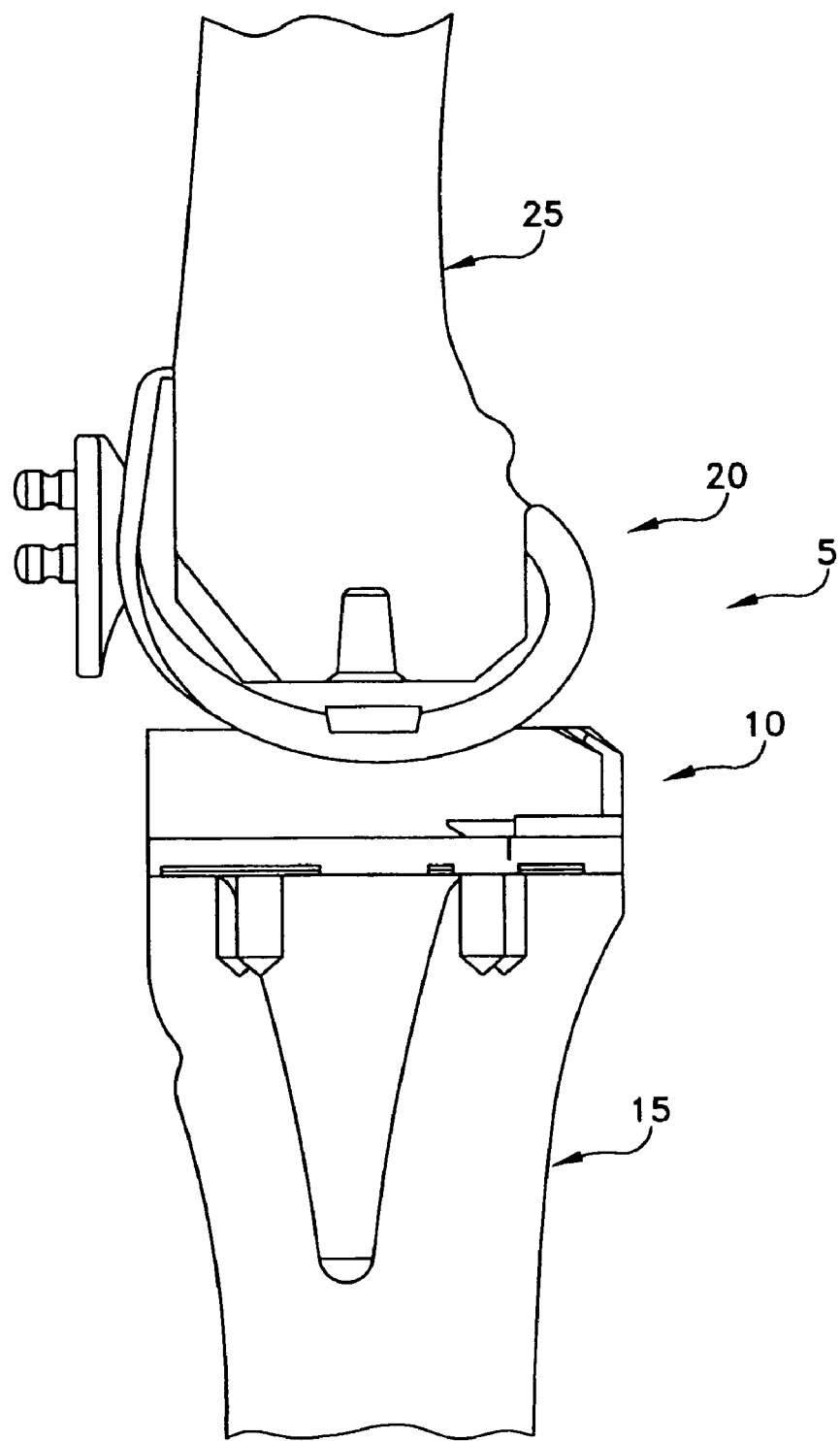
FIG. 1 is a schematic side view showing a prosthetic total knee joint positioned within a patient's body.

Looking first at FIG. 1, there is shown a prosthetic total knee joint 5 which generally comprises a prosthetic tibial component 10 secured to the top end of a resected tibia 15, and a prosthetic femoral component 20 which is secured to the bottom end of a resected femur 25.

Figure 2:
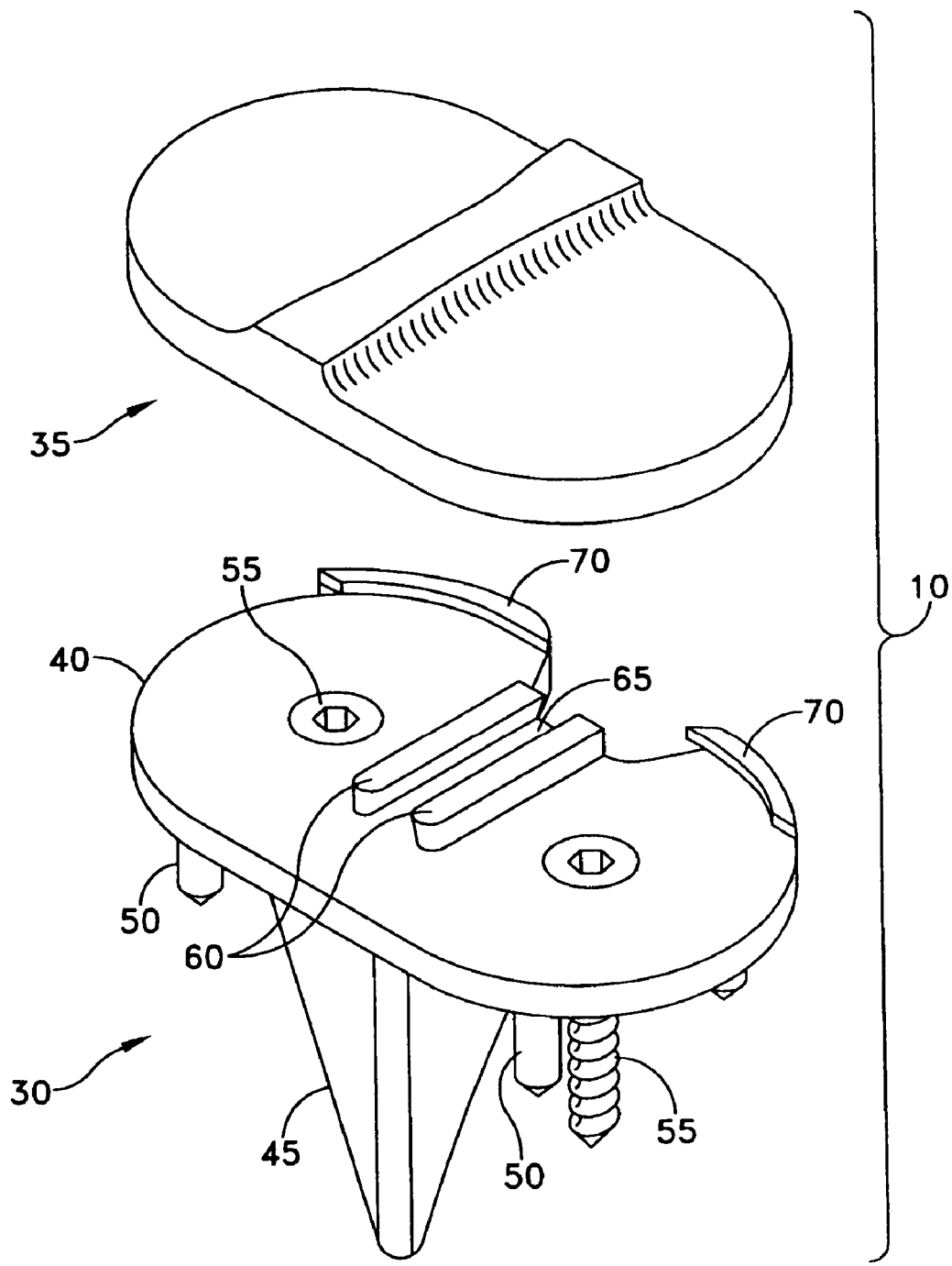
FIG. 2 is an exploded schematic view showing the prosthetic tibial component of the prosthetic total knee joint shown in FIG. 1.
Figure 3:
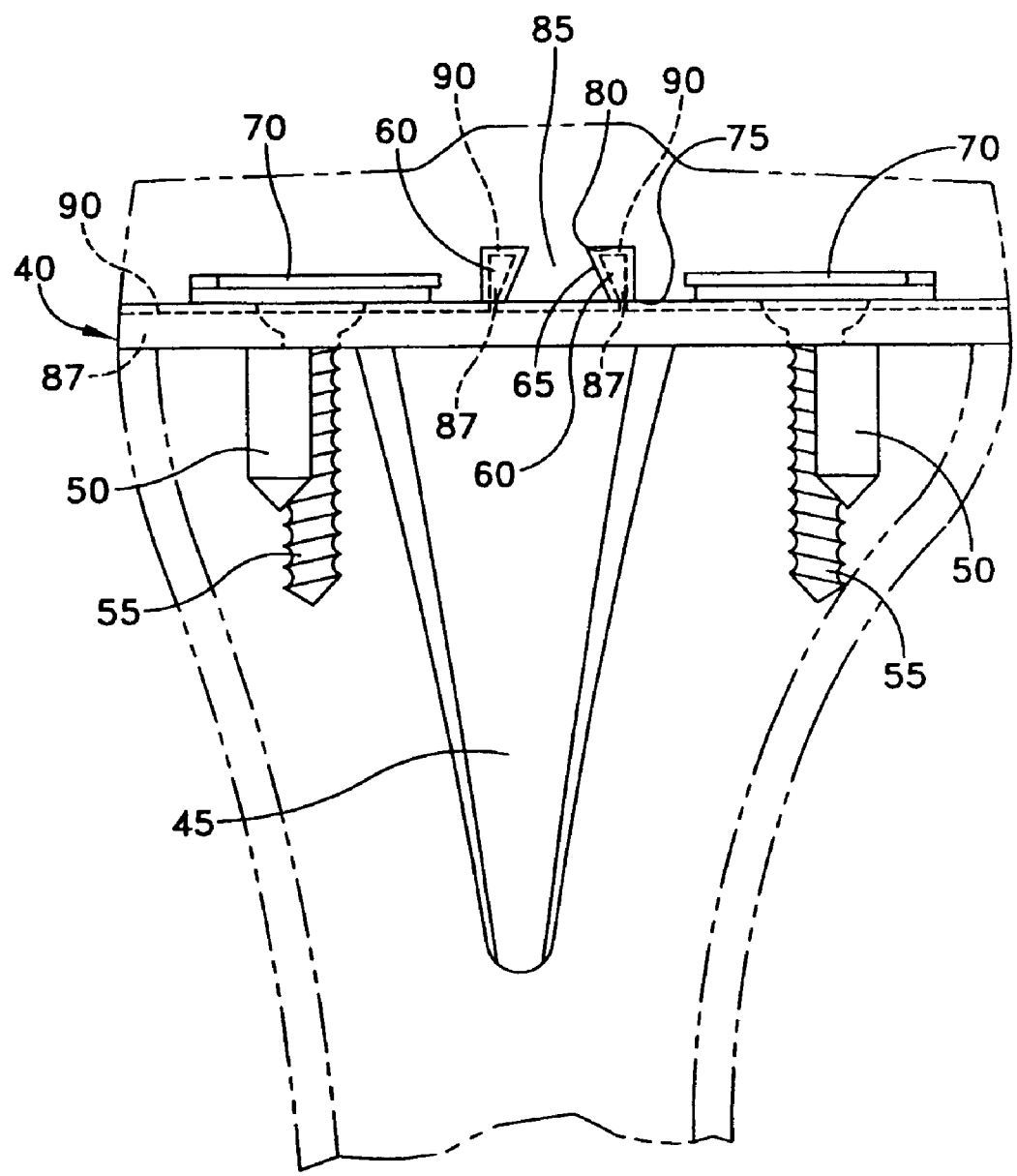
FIG. 3 is a schematic side view of the prosthetic tibial component of the prosthetic total knee joint shown in FIG. 1.

Prosthetic tibial component 10 is shown in greater detail in FIGS. 2 and 3. Prosthetic tibial component 10 generally comprises a metal base construct 30 and a polyethylene bearing construct 35.

More particularly, metal base construct 30 comprises a base plate 40, a stem 45 and a plurality of pegs 50 descending from base plate 40, a plurality of screws 55 passing through base plate 40, a pair of rails 60 running along the top surface of base plate 40 and defining a groove 65 therebetween, and a pair of end walls 70 connected to base plate 40.

Polyethylene bearing construct 35 comprises a flat bottom surface 75 having a longitudinally-extending recess 80 in which is disposed a longitudinally-extending tongue 85. Tongue 85 is sized to slidingly fit in the groove 65 of metal base construct 30, whereby polyethylene bearing construct 35 may be secured to metal base construct 30.

In use, the top end of tibia 15 is resected, metal base construct 30 is secured to tibia 15 via screws 55, and polyethylene bearing construct 35 has its tongue 85 slid into groove 65 until polyethylene bearing construct 35 engages the base plate's end walls 70.

In accordance with the present invention, metal base construct 30 is formed with a bimetal construction. More particularly, the metal base construct 30 is composed of two different metals, a first metal 87 which engages tibia 15 and a second metal 90 which engages polyethylene bearing construct 35. Each of these metals is selected so that its characteristics are well suited to its particular function. More particularly, first metal 87 (i.e., the one that engages tibia 15) is selected so as to provide a superior bone-engaging face, while second metal 90 (i.e., the one that engages polyethylene bearing construct 35) is selected so as to provide a superior polyethylene-engaging face. By combining the different material characteristics of two different metals in base metal construct 30, it is possible to simultaneously form a superior bone-engaging face and a superior polyethylene-engaging face. Among other things, by selecting two approingrowth can be achieved while still avoiding the aforementioned problems with "backside wear".

For instance, a base metal construct 30 may be formed whose bone-engaging surfaces are formed from titanium and whose polyethylene-engaging surfaces are formed from CoCrMo. This construction places a good bone ingrowth metal against the bone and a good polyethylene-engaging metal against the polyethylene, whereby to provide a significantly superior prosthetic tibial component 10.

It is also possible to use other metals that are suitable in both strength, biocompatibility, and joinability to make the bimetal tibial component construct.

By way of example but not limitation, first metal 87 may comprise titanium, titanium alloys, tantalum, tantalum alloys or other metals and/or metal alloys consistent with the present invention. Among other things, first metal 87 is preferably a material which is highly biocompatible and which exhibits good bone ingrowth properties.

By way of further example but not limitation, second metal 90 may comprise CoCrMo, cobalt based alloys, stainless steels, zirconium based alloys or other metals and/or metal alloys consistent with the present invention. Among other things, second metal 90 is preferably a material which has relatively high hardness and which is scratch resistant.

For the purposes of the present invention, the term bimetal may be defined as a composite of two metals, where each of the metals has a different primary constituent. The bimetal construct can be formed from two different commercially pure metals, from two alloys of different base metals, or a combination thereof.

The bimetal construct can be fabricated using a variety of techniques. In one preferred form of the invention, the bimetal construct is fabricated using the method disclosed in pending U.S. patent application Ser. No. 09/079,502, which patent application is hereby incorporated herein by reference. Alternatively, the bimetal construct can be fabricated by other techniques such as plasma spray, diffusion bonding, sintering, or metallurgical methods, e.g., such as a method of the sort disclosed in U.S. Pat. No. 5,323,954 (Shetty).

What is claimed is:

1. A prosthetic tibial component for a prosthetic total knee joint, said component comprising:
    first and second constructs;
    said first construct comprising a metal base construct adapted to engage a tibia; and
    said second construct comprising a polyethylene bearing construct that attaches to said metal base construct and articulates with a prosthetic femoral component on an opposing side of the joint;
    wherein said metal base construct comprises first and second different metals;
    said first metal being adapted to engage a tibia surface; and
    said second metal being adapted to engage said polyethylene bearing construct;
    said first metal being adapted to provide a superior bone-engaging face; and
    said second metal being adapted to provide a superior polyethylene-engaging face.

2. A prosthetic tibial component according to claim 1 wherein said first metal comprises a material which is biocompatible and exhibits bone ingrowth properties.

3. A prosthetic tibial component according to claim 2 wherein said first metal comprises a selected one of a group of metals consisting of titanium, titanium alloy, tantalum, and tantalum alloy.

4. A prosthetic tibial component according to claim 1 wherein said second metal comprises a material which exhibits high hardness and is scratch resistant.

5. A prosthetic tibial component according to claim 4 wherein said second metal comprises a selected one of a group of materials consisting of stainless steel, a cobalt based alloy, a zirconium based alloy, and CoCrMo.

6. A prosthetic tibial component in accordance with claim 1 wherein said metal base construct comprises:
    a base plate having said first metal on a first surface thereof for engagement with the tibia;
    a stem extending from the first surface and adapted to be embedded in the tibia;
    posts extending from the first surface of said base plate for connecting engagement with the tibia; and
    a connector disposed on a second surface of said base plate for connection to a complementary connector on the polyethylene bearing construct.

7. The prosthetic tibial component in accordance with claim 6 wherein said connectors comprise tongue-in-groove connectors.

* * * * *